US00PP30889P2

(12) United States Plant Patent
Kolster

(10) Patent No.: US PP30,889 P2
(45) Date of Patent: Sep. 24, 2019

(54) ***CALLICARPA* PLANT NAMED 'KOLMSQUEEN'**

(50) Latin Name: *Callicarpa bodinieri*
Varietal Denomination: Kolmsqueen

(71) Applicant: Kolster Holding BV, Boskoop (NL)

(72) Inventor: Peter R. Kolster, Boskoop (NL)

(73) Assignee: KOLSTER HOLDING B.V., Boskoop (NL)

( * ) Notice: Subject to any disclaimer, the term of this patent is extended or adjusted under 35 U.S.C. 154(b) by 0 days.

(21) Appl. No.: 15/932,409

(22) Filed: Feb. 27, 2018

(51) Int. Cl.
*A01H 5/08* (2018.01)
*A01H 6/50* (2018.01)

(52) U.S. Cl.
USPC ..... Plt./226
CPC ..... *A01H 5/08* (2013.01); *A01H 6/50* (2018.05)

(58) Field of Classification Search
USPC ..... Plt./226
See application file for complete search history.

*Primary Examiner* — Anne Marie Grunberg
(74) *Attorney, Agent, or Firm* — Penny J. Agyuirre

(57) ABSTRACT

A new cultivar of *Callicarpa* plant, 'Kolmsqueen', that is characterized by its abundance of white berries, its compact plant habit, its berries that are large in size and borne in round clusters, and its compact plant habit.

2 Drawing Sheets

Genus/species: *Callicarpa bodinieri.*
Varietal denomination: 'Kolmsqueen'.

BACKGROUND OF THE INVENTION

The present invention relates to a new and distinct cultivar of *Callicarpa bodinieri* and will be referred to hereafter by its cultivar name, 'Kolmsqueen'. 'Kolmsqueen' represents a new cultivar of beautyberry; a deciduous shrub grown for landscape use.

The new *Callicarpa* arose from a breeding program conducted by the Inventor in Boskoop, The Netherlands. The objective of the breeding program was to develop new cultivar of *Callicarpa* with large white berries that is suitable as a garden plant.

The new *Callicarpa* originated from open pollination in June of 2009 of an unnamed and unpatented plant of *Callicarpa* from the Inventor's breeding program, designated as 715B. 'Kolmsqueen' was selected as a single unique plant in 2014 from the resulting seedlings.

Asexual propagation of the new cultivar was first accomplished by stem cuttings in February 2012 in Boskoop, The Netherlands under the direction of the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new *Callicarpa*. These attributes in combination distinguish 'Kolmsqueen' as a unique and distinct cultivar of *Callicarpa.*

1. 'Kolmsqueen' exhibits an abundance of white berries.
2. 'Kolmsqueen' exhibits berries that are large in size and borne on round clusters.
3. 'Kolmsqueen' exhibits a compact plant habit.

The female parent of 'Kolmsqueen' differs from 'Kolmsqueen' in having a less compact plant habit and berries that are purple in color. 'Kolmsqueen' is most closely compared to *Callicarpa dichotoma* 'Albifructus' (not patented) and *Callicarpa japonica* 'Leucocarpa' (not patented). 'Albifructus' is similar to 'Kolmsqueen' in having an upright plant habit and berries that are white in color. 'Albifructus' differs from 'Kolmsqueen' in having a less compact plant habit and berry clusters that are flattened in shape. 'Leucocarpa' is similar to 'Kolmsqueen' in having berries that are white in color. 'Leucocarpa' differs from 'Kolmsqueen' in having less berries that are smaller in size and in having less compact and a plant habit with trailing branches.

BRIEF DESCRIPTION OF THE DRAWINGS

The accompanying photographs were taken of a three year-old plant of 'Kolmsqueen' as grown outdoors in a trial bed in Boskoop, The Netherlands.

The photograph in FIG. 1 was provides a view of the plant habit of 'Kolmsqueen'.

Figure 1:
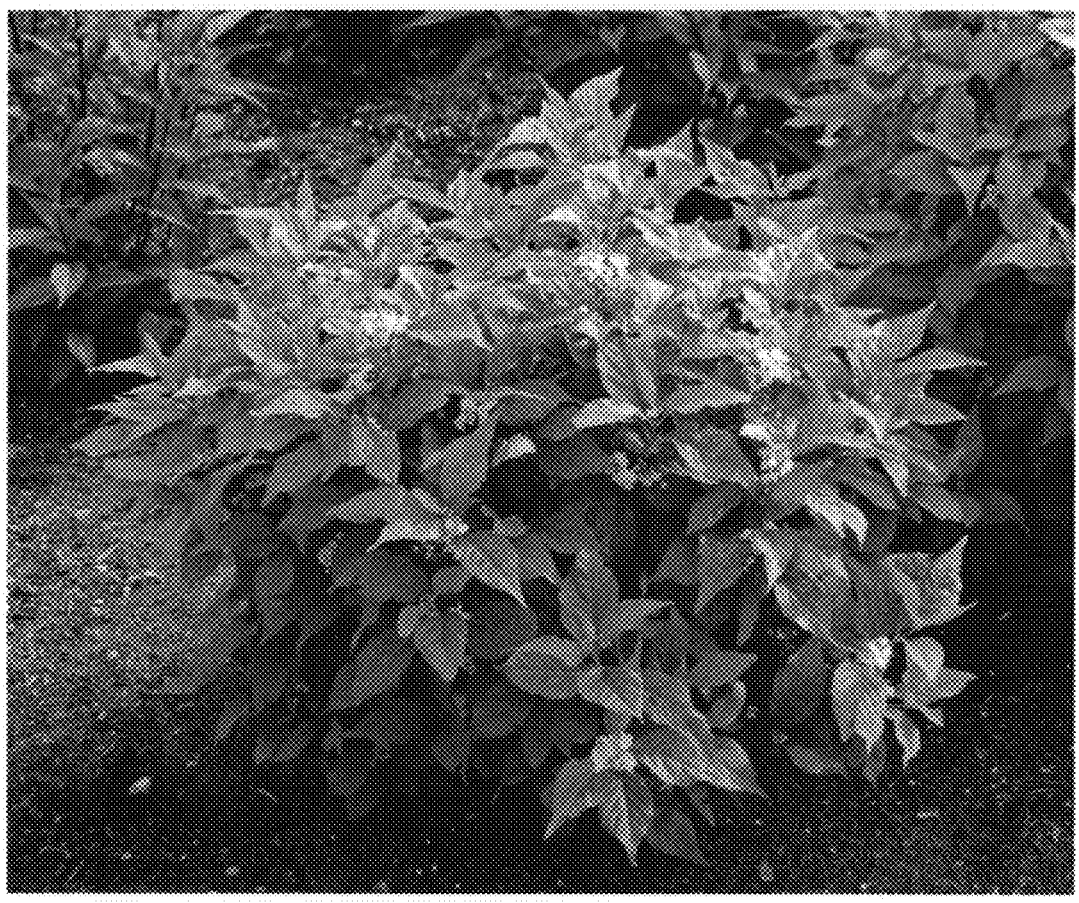
Figure 2:
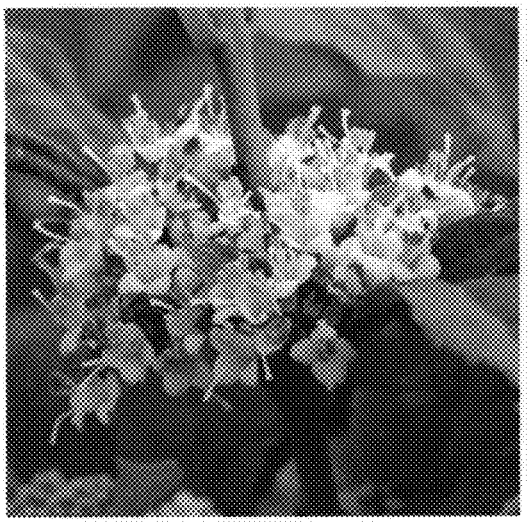

The photograph in FIG. 2 provides a close-up view of an inflorescence of 'Kolmsqueen'.

Figure 3:
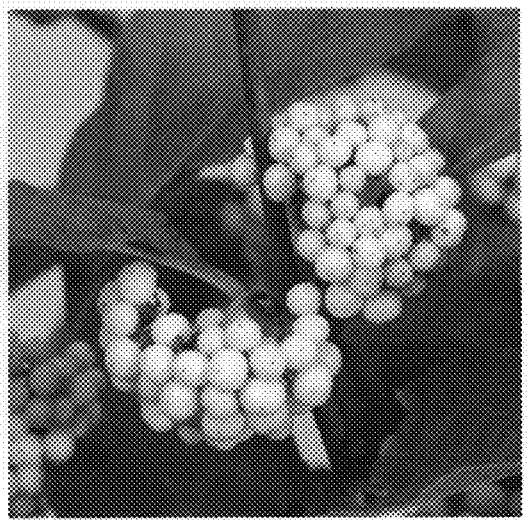

The photograph in FIG. 3 provides a close-up view of the berries of 'Kolmsqueen'.

Figure 4:
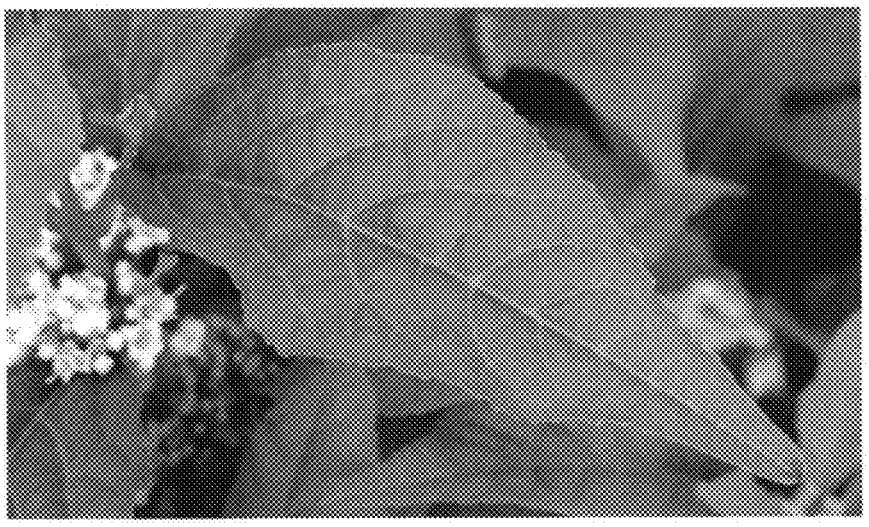

The photograph in FIG. 4 provides a close-up view of the leaves of 'Kolmsqueen'.

The colors in the photographs are as close as possible with the digital photography and printing techniques utilized and the color codes in the detailed botanical description accurately describe the colors of the new *Callicarpa.*

BOTANICAL DESCRIPTION OF THE PLANT

The following is a detailed description of 3 year-old plants of the new cultivar as grown outdoors in a field in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—From June to October in The Netherlands.

*Plant type.*—Deciduous shrub.

*Plant habit.*—Broad upright.

*Height and spread.*—An average of 70.8 cm in height (soil level to top of foliar plane), average of 66.5 cm in height (soil level to top of floral plane) and 80.3 cm in spread.

*Hardiness.*—At least in U.S.D.A. Zones 6 to 9.

*Diseases.*—No susceptibility or resistance to diseases has been observed.

*Root development.*—Roots initiate in about 20 days and will fully root as a young plant in a 2-inch plug in about 42 days in summer.

*Propagation.*—Stem cuttings.

*Growth rate.*—Moderate to high,

Branch description:

*Branch color.*—Young stems; 144B, mature stems; 144A, bark; 199B.

*Branch shape.*—Circular.

*Branch aspect.*—Average of 40° to vertical.

*Branch size.*—Average of 12.9 cm in length and 2.5 mm in diameter.

*Branch surface.*—Very slightly glossy.

*Branch strength.*—Strong.

*Branching.*—Freely branched, main branches; an average of 20, strong, lateral branches; an average of 10, strong.

*Internode length.*—3.7 cm.

Foliage description:

*Leaf shape.*—Obovate to elliptic.

*Leaf division.*—Simple.

*Leaf base.*—Attenuate.

*Leaf apex.*—Apiculate.

*Leaf venation.*—Pinnate, upper surface; 144A, lower surface; 145C.

*Leaf margin.*—Finely serrate on upper ¾ of leaf.

*Leaf attachment.*—Petiolate.

*Leaf arrangement.*—Opposite.

*Leaf surface.*—Upper surface; very slightly glossy and moderately covered with very short hairs; an average of 0.2 mm in length and too small to measure color, lower surface matte.

*Leaf size.*—An average of 10 cm in length and 4.4 cm in width.

*Leaf number.*—Average of 12 per lateral branch.

*Leaf color.*—Young leaves upper surface; 144A, young leaves lower surface; 144B, mature leaves upper surface; color between 143A and 146A, autumn color 154B to 154D, mature leaves lower surface; 146B, autumn color N144A.

*Petioles.*—8 mm in length, 1.5 mm in diameter, medium to high strength, upper surface; 144B in color, matte surface, lower surface; 144C in color, slightly glossy surface.

Flower description:

*Flower type.*—Axillary cyme, upright, funnel form.

*Flower fragrance.*—Moderate, sweet and pleasant.

*Flower lastingness.*—Average of 7 days, self-cleaning.

*Flower bud description.*—Obovate in shape, glabrous, matte and smooth surface, average of 4 mm in length and 2 mm in diameter, color between 155B and 158D with base 144C.

*Flower quantity.*—Freely flowering, about 68 flowers per corymb.

*Inflorescence size.*—Average of 2 cm in height, 2.6 cm in diameter.

*Flower size.*—5 mm in height, 5 mm in diameter, 9 mm in length, throat diameter 1.5 mm, tube length 2 mm, tube diameter at distal end, 2.5 mm, proximal end 1.2 mm.

*Petal description.*—4, 1 whorl, funnel form, rotate, lower 50% of petals fused into a funnel form, 4 mm in length, 2 mm in width, obovate in shape, obtuse apex, base fused, entire margins, both surfaces smooth, glabrous, matte, and slightly velvety, color of upper and lower surfaces when opening and fully open, throat, and tube 155B to 155C.

*Calyx size.*—Rotate, 1.2 mm in length, 1.75 mm in diameter.

*Sepal description.*—4, 1 whorl, broad triangular in shape, margin is entire, apex is broad acute, base 85% fused, surface is glabrous, matte and smooth, an average of 1.2 mm in length and 0.75 mm in width, when opening upper and lower side 144C, fully open upper and lower surface 145B.

*Peduncles.*—Average of 1.2 cm in length and 1 mm in diameter, held in an average angle of 25°, strong, glabrous, smooth and matte surface, 144A in color.

*Pedicels.*—Average of 1.5 cm in length and 0.5 mm in diameter, held in an average angle of 30°, moderately strong, glabrous, smooth and matte surface, 145C in color.

Reproductive organs:

*Gynoecium.*—Pistil; 1, average of 1 cm in length, stigma; 0.5 mm in diameter, club-shaped, cleft, NN155D in color, style; 9 mm in length and NN155C in color, ovary; 145B in color.

*Androecium.*—Stamens; 4, anthers; basifixed, double oblong in shape, 1 mm in length, 0.5 mm in width, 163B to 163C in color, filaments; 4 mm in length, NN155C in color, pollen not observed.

*Fruit and seed.*—Seeds; 4, 3 mm in length, 1.25 mm in diameter, smooth and glabrous surface, 162C in color, fruit; average of 1,500 berries per plant, borne on rounded clusters, 4 mm in length, 5.5 mm in diameter, smooth, glabrous and moderately glossy surface, NN155B to NN155C in color, non-edible, 100 days to fruit ripening, ripen in October, berries last 14 days after ripening.

It is claimed:

1. A new and distinct cultivar of *Callicarpa* plant named 'Kolmsqueen' substantially as herein illustrated and described.

* * * * *